United States Patent
Glassman et al.

(10) Patent No.: US 6,827,943 B2
(45) Date of Patent: Dec. 7, 2004

(54) DERMATOLOGICAL COMPOSITION CONTAINING UREA

(75) Inventors: Bradley P. Glassman, Fairfield, NJ (US); Dileep Bhagwat, Bronxville, NY (US); Daniel Glassman, Fairfield, NJ (US)

(73) Assignee: Bradley Pharmaceuticals, Inc., Fairfield, NJ (US)

( * ) Notice: Subject to any disclaimer, the term of this patent is extended or adjusted under 35 U.S.C. 154(b) by 15 days.

(21) Appl. No.: 10/328,368

(22) Filed: Dec. 23, 2002

(65) Prior Publication Data

US 2004/0122087 A1 Jun. 24, 2004

(51) Int. Cl.$^7$ .............................. A61K 6/00; A61K 7/00
(52) U.S. Cl. ..................... 424/401; 424/70.1; 424/600; 424/630; 424/639; 424/641; 514/844
(58) Field of Search ................................ 424/401, 70.1, 424/600, 630, 639, 641; 514/844

(56) References Cited

U.S. PATENT DOCUMENTS

| | | | | |
|---|---|---|---|---|
| 5,919,470 A | * | 7/1999 | Valdez et al. | ................ 424/401 |
| 6,046,178 A | * | 4/2000 | Silvetti, Sr. | ................. 514/60 |
| 6,281,239 B1 | | 8/2001 | Glassman | |
| 6,380,236 B2 | | 4/2002 | Glassman | |
| 6,429,231 B1 | | 8/2002 | Bhagwat et al. | |
| 6,495,602 B1 | | 12/2002 | Bhagwat et al. | |
| 6,573,301 B1 | | 6/2003 | Glassman et al. | |
| 6,673,842 B2 | | 1/2004 | Bhagwat et al. | |
| 6,743,417 B2 | | 6/2004 | Glassman et al. | |
| 2003/0212127 A1 | | 11/2003 | Glassman et al. | |

* cited by examiner

*Primary Examiner*—Michael G. Hartley
*Assistant Examiner*—Konata M George
(74) *Attorney, Agent, or Firm*—Andrea G. Reister; Covington & Burling

(57) ABSTRACT

Described are dermatological compositions for treating, protecting and re-epitheliazing cutaneous wounds and damaged skin, such compositions including about 21 to about 40% urea and trace amounts of zinc, copper and manganese in the form of their respective pharmaceutically acceptable salts.

26 Claims, No Drawings

DERMATOLOGICAL COMPOSITION CONTAINING UREA

FIELD OF THE INVENTION

This invention relates to a novel composition containing urea and select trace elements for treating, protecting and re-epitheliazation of cutaneous wounds and damaged skin.

BACKGROUND OF THE INVENTION

Urea has been long recognized as a cosmetic ingredient in formulations acting as a humectant and moisturizer. Urea is also recognized as a medically useful keratolytic agent because of urea's ability at high concentrations to solubilize and denature protein. High concentrations of urea are also known to have an antibacterial effect.

U.S. Pat. No. 5,919,470 describes dermatological compositions using high concentrations of urea for treating xerosis and other skin conditions. This patent is being incorporated herein by reference.

Urea is known to have a strong proteolytic action and is an effective keratolytic agent particularly at an optimal concentration of 40%. Urea is very effective in dispersing epidermal keratin. Urea is non-toxic even at these high concentrations.

Trace elements play an important role in the biochemistry of living organisms including wound healing and healthy skin. Removal of necrotic tissue from wounds is essential to facilitate wound healing. Eschar and devitalized tissue may be removed by sharp, autolytic, enzymatic or surgical debridement. Urea is an excellent chemical debridement agent and can be applied directly to the wound became it is non-toxic.

Wound healing is promoted through maintenance of a moist environment and an environment which prevents microbial contamination. Both these essential wound healing aspects are provided by urea, as urea has good antimicrobial properties and can entrap water in the wound tissue/skin. Besides urea is an excellent chemical debridement agent particularly for eschar and devitalized skin and nail.

Trace amounts of zinc, copper and manganese are known to help in accelerating the healing of cutaneous wounds. Although the mechanism by which this is achieved is not clearly understood, these trace elements accelerate the re-epitheliazation of cutaneous wounds. Zinc, copper and manganese promote keratoinocyte proliferation.

There remains a need in the industry to improve upon compositions used in wound healing and repairing damaged skin.

SUMMARY OF THE INVENTION

We have found that combining urea and trace amounts of zinc, copper and manganese in a dermatological composition provides a novel approach for treating, protecting and re-epitheliazation of cutaneous wounds and the skin.

Accordingly, the present invention includes an improved method of treatment of a variety of dermatoses characterized by dry scaly skin, and cutaneous wounds using concentrations of about 21 to about 40 wt-% of urea in a suitably defined formulation containing trace elements of zinc, copper and manganese.

Thus, one aspect of the present invention is a dermatological composition including from about 21 to about 40 wt-% urea and trace elements of zinc, copper and manganese and the balance being dermatologically acceptable excipients.

The use of such high concentrations of urea combined with skin protectants of an oleaginous nature derived from petroleum and further combined with suitable emulsifiers and thickeners have been found to be effective for treating dermatological conditions manifested by dry scaly skin and cutaneous wounds without the need of traditional preservatives.

Accordingly, another aspect of the present invention is a dermatological composition including:

a) about 21 to about 40 wt-% urea;
b) trace amounts of zinc (1 ppm to 0.2%)
c) trace amounts of copper (1 ppm to 0.2%)
d) trace amounts of manganese (1 ppm to 0.2%)
e) about 5.5 to about 20 wt-% petrolatum or a synthetic or semi-synthetic hydrocarbon, or a semi-solid mixture thereof;
f) about 10 to about 20 wt-% of a liquid petrolatum or a synthetic or semi-synthetic oleaginous liquid fraction, or a mixture thereof;
g) about 0.25 to about 2 wt-% of C16–18 aliphatic straight or branched chain fatty alcohol or fatty acid, or a mixture thereof;
h) about 1 to about 5 wt-% propylene glycol;
i) about 1 to about 3 wt-% glyceryl stearate;
j) about 0.01 to about 0.5 wt-% xanthum gum; and
k) the balance being water.

Still another embodiment of the invention includes a dermatological composition containing:

a) about 21 to about 40 wt-% urea;
b) trace amounts of zinc (1 ppm to 0.2%)
c) trace amounts of copper (1 ppm to 0.2%)
d) trace amounts of manganese (1 ppm to 0.2%)
e) about 5.5 to about 20 wt-% petrolatum or a synthetic or semi-synthetic hydrocarbon, or a semi-solid mixture thereof;
f) about 10 to about 20 wt-% of a liquid petrolatum or a synthetic or semi-synthetic oleaginous liquid fraction, or a mixture thereof;
g) about 0.25 to about 2 wt-% of a C16–18 aliphatic straight or branched chain fatty alcohol or fatty acid, or a mixture thereof;
h) about 1 to about 5 wt-% propylene glycol;
i) about 1 to about 2 wt-% glyceryl stearate;
j) about 0.01 to about 0.5 wt-% xanthan gum;
k) about 0.05 to about 30 wt-% of a mixture of a carbomer and triethanolamine; and the balance being water.

Still another aspect of the present invention is a method of treating skin and cutaneous wounds by applying to an affected area in need of treatment an effective amount of a semi-solid dermatological composition containing about 21 to about 40 wt-% urea and trace amounts of zinc, copper and manganese as their respective pharmaceutically acceptable, i.e., bio-compatible salts.

DETAILED DESCRIPTION

The dermatological composition of the present invention is a semi-solid at room temperature. A preferred application of the formulation is a cream which contains a petroleum based liquid and solid fraction as skin protectants when applied to skin. A preferred application of the formulation is for application to cutaneous wounds and damaged skin.

The cream composition has advantageous properties for the treatment of dry scaly skin clinically characterized as xerosis and for the temporary relief of itching associated with various pathological dermatological conditions. The formulation produces a keratolytic action found beneficial in the treatment of ichthyosis, psoriasis and atopic dermatitis. Application of the cream to the skin as needed provides relief of the conditions.

Trace amounts of the zinc, copper and manganese metals range in the composition from about 1 part per million (ppm) to about 0.2 wt-%, or from about 10 ppm to about 0.2 wt-%, of active metal sourced from its corresponding pharmaceutically acceptable, bio-compatible salts. Examples of bio-compatible salts of manganese are manganese carbonate, chloride, gluconate, glycerophosphate, lactate, or nitrate. Examples of copper bio-compatible salts include copper acetate, bromide, carbonate, chloride, citrate, gluconate, glycinate, iodide or nitrate. Bio-compatible zinc salts include but are not limited to zinc acetate, bromide, carbonate, chloride, citrate, gluconate, glycinate, lactate, nitrate, or sulfate. The preferred salts for these metals are the gluconate salts. These salts are commercially available, for example, from Spectrum Chemical and Laboratory Products, Gardena, Calif.

In addition to containing about 21 to about 40 wt-% of urea and trace amounts of zinc, copper and manganese as their bio-compatible salts, the composition of the present invention includes skin protectants which include a combination of semi-solid and liquid petroleum fractions. The semi-solid skin protectant is contained in about 5.5 to about 20 wt-% and includes petrolatum or a synthetic or semi-synthetic hydrocarbon of the same nature as petrolatum. Mixtures of such ingredients can also be used. The preferred semi-solid material is petrolatum, commercially available from a wide variety of sources.

The liquid portion skin protectant is a liquid petrolatum and contained in the composition in about 5 to about 30 wt-%. This material can include any synthetic or semi-synthetic oleaginous liquid fraction. A preferred embodiment is mineral oil which is a liquid mixture of hydrocarbons obtained from petroleum.

Another preferred ingredient encompassed in the composition of the present invention is propylene glycol which may be contained up to about 5 wt-% in the composition, preferably in the range of from about 1 to about 5 wt-%.

Although not to be held by theory, it is believed that the mild antibacterial properties of the urea and propylene glycol allow the composition of the present invention to be free of conventional preservatives such as methyl paraben, propyl and butyl imidazolidinylurea, diazolidinylurea, methylchloroisothiazolinone and methylisothiazolinone.

In addition to the above embodiments, the present composition also contains dermatologically acceptable excipients, such as for example emulsifiers and thickeners. Among these are, for example, C16 to C18 straight or branched chain fatty alcohols or fatty acids or mixtures thereof. Preferably these include cetyl alcohol, stearyl alcohol, stearic acid, palmitic acid, or mixtures thereof. Fatty acids or fatty alcohols may be present in from about 0.25 to 2 wt-%.

Another ingredient useful in the composition of the present invention may be glyceryl stearate, which is a monoester of glycerine and stearic acid, or other suitable forms of glyceryl stearate, for example glyceryl stearate SE, which is a commercially available self-emulsifying grade of glycerol stearate that contains some sodium and/or potassium stearate. Glyceryl stearate may be in the composition anywhere from about 1 to about 3 wt-%.

Xanthan gum is another ingredient which may be used in the present invention. Xanthan gum is a high molecular weight heteropolysaccharide gum produced by pure-culture fermentation of a carbohydrate with Xanthomonas campestris. The gum is also commercially available from various sources.

As part of the dermatologically acceptable excipients, the composition includes thickeners which provide a high viscosity cream designed to remain in place upon application to the skin. Preferred thickeners include a mixture of triethanolamine and a carbomer combined together and added to the composition in an amount totaling anywhere from about 0.05 to 30 wt-%. Triethanolamine is purchased as Trolamine NF from BASF. The carbomers come in various molecular weights and identified by numbers. These are otherwise known as Carbopol. A preferred embodiment of the present invention is Carbopol 940. The carbomer or Carbopols are resins which are known thickening agents. They are homopolymers of acrylic acid crosslinked with an allyl ether of pentaerythritol, an allyl ether of sucrose or an allyl ether of propylene. The carbomer is present in the composition as a thickener and also is used to suspend and stabilize the emulsion. Although Carbopol 940 is preferably used in the present invention, other analogs may also be used such as Carbomer 910, 2984, 5984, 954, 980, 981, 941 and 934. Carbopol ETD 2001, 2020, and 2050 and Ultrez 20 are also commercially available and can be used since they are similar in chemistry and function.

A typical formulation representing a particular embodiment of the present invention is illustrated as follows:

| Ingredient | % w/w |
| --- | --- |
| Purified water | 36.149 |
| Urea, USP | 40.000 |
| Zinc (as bio-compatible Salt) | Trace* |
| Copper (as bio-compatible Salt) | Trace* |
| Manganese (as bio-compatible Salt) | Trace* |
| Carbopol 940 | 0.150 |
| Petrolatum | 5.940 |
| Mineral oil | 12.060 |
| Glyceryl stearate | 1.875 |
| Cetyl alcohol | 0.626 |
| Propylene glycol | 3.000 |
| Xanthan gum | 0.050 |
| Trolamine NF | 0.150 |
| TOTAL | 100.000 |

*1 ppm to 0.2 wt-% as active metal in the salt

Glossary of Ingredients

The formulation of the present invention has been defined above and more specifically exemplified in the following examples. Since the formulation employs various ingredients, some of the ingredients have been defined generically and by common name. In addition, the following is a glossary of technical names and trade names with manufacturing sources for some of the ingredients employed in the formulation of the present invention.

Mineral Oil

Definition

Mineral oil is a liquid mixture of hydrocarbons obtained from petroleum.

Technical Names

Heavy Mineral Oil

Light Mineral Oil

Liquid Paraffin
Paraffin Oil
Trade Names
Benol White Mineral Oil (Witco/Sonneborn)
Blandol White Mineral Oil (Witco/Sonneborn)
Britol 6 (Witco Corporation)
Britol 7 (Witco Corporation)
Britol 9 (Witco Corporation)
Britol 20 (Witco Corporation)
Britol 24 (Witco Corporation)
Britol 35 (Witco Corporation)
Britol 50 (Witco Corporation)
Carnation White Mineral Oil (Witco/Sonneborn)
Crystosol NF 70 (Witco Corporation)
Crystosol NF 90 (Witco Corporation)
Crystosol USP 200 (Witco Corporation)
Crystosol USP 240 (Witco Corporation)
Crystosol USP 350 (Witco Corporation)
Drakeol 5 (Penreco)
Drakeol 6 (Penreco)
Drakeol 7 (Penreco)
Drakeol 8 (Penreco)
Drakeol 9 (Penreco)
Drakeol 10 (Penreco)
Drakeol 13 (Penreco)
Drakeol 15 (Penreco)
Drakeol 19 (Penreco)
Drakeol 21 (Penreco)
Drakeol 32 (Penreco)
Drakeol 34 (Penreco)
Drakeol 35 (Penreco)
Draketex 50 (Penreco)
Ervol White Mineral Oil (Witco/Sonneborn)
Gloria White Mineral Oil (Witco/Sonneborn)
Kaydol White Mineral Oil (Witco/Sonneborn)
Klearol White Mineral Oil (Witco/Sonneborn)
Parol 70 (Penreco)
Parol 80 (Penreco)
Parol 100 (Penreco)
PD-23 White Mineral Oil (Witco/Sonneborn)
Peneteck (Penreco)
Protol White Mineral Oil (Witco/Sonneborn)
Superla Mineral Oil #5 NF (Amoco Lubricants)
Superla Mineral Oil #6 NF (Amoco Lubricants)
Superla Mineral Oil #7 NF (Amoco Lubricants)
Superla Mineral Oil #9 NF (Amoco Lubricants)
Superla Mineral Oil #10 NF (Amoco Lubricants)
Superla Mineral Oil #13 NF (Amoco Lubricants)
Superla Mineral Oil #18 NF (Amoco Lubricants)
Superla Mineral Oil #21 NF (Amoco Lubricants)
Superla Mineral Oil #31 NF (Amoco Lubricants)
Superla Mineral Oil #35 NF (Amoco Lubricants)
Uniwhite Oil 55 (UPI)
Uniwhite Oil 70 (UPI)
Uniwhite Oil 85 (UPI)
Uniwhite Oil 130 (UPI)
Uniwhite Oil 185 (UPI)
Uniwhite Oil 205 (UPI)
Uniwhite Oil 350 (UPI)
Glyceryl Stearate
Empirical Formula $C_{21}H_{42}O_4$ Definition
Glyceryl stearate is the monoester of glycerin and stearic acid. It conforms generally to the formula:

$CH_3(CH_2)_{16}COOCH_2CN(OH)CH_2OH$

Technical Names
2.3-Dihydroxypropyl octadecanoate
Glyceryl monostearate
Monostearin
Octadecanoic acid, 2.3-dihydroxypropyl ester
Octadecanoic acid, monoester with 1,2,3-propanetriol
Trade Names
Aldo HMS (Lonza Inc./Lonza Ltd.)
Aldo MS (Lonza Inc./Lonza Ltd.)
Aldo MSLG (Lonza Inc./Lonza Ltd.)
Alkamuls GMS (Rhone-Poulenc)
Arlacel 129 (ICI)
Atmos 150 (ICI)
Atmul 84 (ICI)
Atmul 124 (ICI)
Capmul GMS (Karishamns Lipid Specialties)
Ceral MN (Fabriquimica)
Ceral MNT (Fabriquimica)
Cerasynt GMs (ISP Van Dyk)
Cerasynt SD (ISP Van Dyk)
Cithrol GMS N/E (Croda Surfactants Ltd.)
CPH-53-N (Hall)
CPH-144-N (Hall)
Cutina GMS (Henkel)
Cutina MD (Henkel)
Cutina MD-A (Henkel)
Dimodan PM (Grinsted)
Dimodan PM 300 (Grinsted)
Elfacos GMS (Akzo BV)
Emerest 2400 (Henkel/Organic Products)
Empilan GMS NSE (Albright & Wilson)
Emuldan FP 40 (Grinsted)
Emuldan HA 60 (Grinsted)
Emuldan HLT 40 (Grinsted)
ESTOL GMS90 1468 (Unichema)
ESTOL GMSveg 1474 (Unichema)
Geleol (Gattefosse)
Grillomuls S 40 (Grillo-Werke)
Grillomuls S 60 (Grillo-Werke)
Grillomuls S 90 (Grillo-Werke)
Hefti GMS-33 (Hefti)
Hodak GMS (Calgene)
Imwitor 191 (Huls AG/Huls America)
Imwitor 900 (Huls AG/Huls America)
Kemester 5500 (Witco)
Kemester 6000 (Witco)

Kessco GMS (Akzo BV)
Lanesta 24 (Lanaetex)
Lasemul 92 AE (Industrial Quimica)
Lasemul 92 AE/A (Industrial Quimica)
Lasemul 92 N 40 (Industrial Quimica)
Lexemul 503 (Inolex)
Lexemul 515 (Inolex)
Lexemul 55G (Inolex)
Lipo GMS 410 (Lipo)
Lipo GMS 450 (Lipo)
Lipo GMS 600 (Lipo)
Nikkol MGS-DEX (Nikko)
Norfox GMS (Norman, Fox & Co.)
Norfvox GMS-SE (Nornan, Fox & Co.)
Prodhybase GLA (Prod'Hyg)
Protachem 26 (Protameen)
Protechem G 5509 (Protameen)
Protechem GMS-540 (Protameen)
Protechem HMS (Protameen)
Sterol GMS (Auschem)
Tegin 90 (Goldschmidt)
Tegin 515 (Goldschmidt)
Tegin 4011 (Goldschmidt)
Tegin 4100 (Goldschmidt)
Tegin GRB (Goldschmidt)
Tegin ISO (Goldschmidt)
Tegin M (Goldschmidt)
Tegin MAV (Goldschmidt)
Unitina MD (UPI)
Unitina MD-A (UPI)
Unitolate GS (UPI)
Witconol 2400 (Witco)
Witconol 2401 (Witco)
Witconol MST (Witco SA)
Witconol MST (Witco)
Zohar GLST (Zohar)
Definition
Glyceryl stearate SE is a self-emulsifying grade of glyceryl stearate (q.v.) that contains some sodium and/or potassium stearate.
Trade Names
Aldo MSD (Lonza Inc./Lonza Ltd.)
Ceral ME (Fabriquimica)
Ceral MET (Fabriquimica)
Ceral TN (Fabriquimica)
Cerasynt Q (ISP Van Dyk)
Cithrol GMS S/E (Croda Surfactants Ltd.)
Cutina KD-16 (Henkel)
Dermalcare GMS/SE (Rhone-Poulenc)
Dracorin GMS SE O/W 2/008475 (Dragoco)
Emerest 2407 (Henkel/Organic Products)
Empilan GMS SE (Albright & Wilson)
Emuldan HA 32/S3 (Grinsted)
ESTOL BMSse 1462 (Unichema)
Hefti GMS-33-SES (Hefti)
Hodag GMS-D (Calgene)
Imwitor 960 (Huls Ag/Huls America)
Kemester 6000 SE (Witco)
Lamecreme KSM (Grunau)
Lanesta 40 (Lanaetex)
Lexemul 530 (Inolex)
Lexemul T (Inolex)
Lipo GMS 470 (Lipo)
Mazol GMSD-K (PPG)
Prodhybase GLN (Prod'Hyg)
REWOMUL MG SE (Rewo Chemische)
Tegin (Goldschmidt)
Tegin Spezial (Goldschmidt)
Tegin V (Goldschmidt)
Unitolate GMS-D (UPI)
Witconol 2407 (Witco)

Cetyl Alcohol
Empirical Formula $C_{16}H_{34}O$

Definition
Cetyl alcohol is the fatty alcohol that conforms generally to the formula:

$CH_3(CH_2)_{14}CH_2OH$

Technical Names
1-Hexadecanol
n-Hexadecyl alcohol
Palmityl alcohol
Trade Names
Adol 52 (Witco)
Adol 520 (Witco)
Adol 52-NF (Witco)
Adol 520-NF (Witco)
Cachalot C-50 (Michel)
Cachalot C-51 (Michel)
Cachalot C-52 (Michel)
Cetaffine (Laserson & Sabetay)
Cetal (Amerchol)
Cetyl Alcohol (Rhone-Poulenc)
CO-1695 (Procter & Gamble)
Crodacol C-70 (Croda Chemicals, Inc.)
Crodacol C90 (Croda Chemicals Ltd.)
Crodacol C-95 (Croda, Inc.)
Fancol CA (Fanning)
Hyfatol 16-95 (Aarhus)
Hyfatol 16-98 (Aarhus)
Lanette 16 (Henkel)
Lanol C (SEPPIC)
Laurex 16 (Albright & Wilson)
Lipocol C (Lipo)

Stearic Acid
Empirical Formula $C_{18}H_{36}O_2$

Definition
Stearic acid is the fatty acid that conforms generally to the formula:

$CH_3(CH_2)_{16}COOH$

Trade Names
Crosterene SA4310 (Croda Universal Ltd.)
Dar-Chem 14 (Darling)
Emersol 120 (Henkel/Emery)
Emersol 132 (Henkel/Emery)
Emersol 150 (Henkel/Emery)
Glycon DP (Lonza Inc./Lonza Ltd.)
Glycon P-45 (Lonza Inc./Lonza Ltd.)
Glycon S-65 (Lonza Inc./Lonza Ltd.)
Glycon S-70 (Lonza Inc./Lonza Ltd.)
Glycon S-90 (Lonza Inc./Lonza Ltd.)
Glycon TP (Lonza Inc./Lonza Ltd.)
Hy-Phi 1199 (Darling)
Hy-Phi 1303 (Darling)
Hy-Phi 1401 (Darling)
Hystrene 4516 (Witco)
Hystrene 5016 (Witco)
Hystrene 7018 (Witco)
Hystrene 9718 (Witco)
Industrene 5016 (Witco)
Industrene 7018 (Witco)
Karacid 1890 (Akzo BV)
Neo-Fat 18 (Akzo)
Neo-Fat 18-54 (Akzo)
Neo-Fat 18-55 (Akzo)
Neo-Fat 18-61 (Akzo)
Pearl Stearic (Darling)
PRIFAC 2981 (Unichema)
Pristerene 4900 (Unichema)
Pristerene 4901 (Unichema)
Pristerene 4902 (Unichema)
Pristerene 4904 (Unichema)
Pristerene 4905 (Unichema)
Pristerene 4910 (Unichema)
Pristerene 4911 (Unichema)
Pristerene 4915 (Unichema)
Pristerene 4921 (Unichema)
Pristerene 4968 (Unichema)
Pristerene 9550 (Unichema)
Safacid 18 (Pronova)
Safacid 16/18 CR (Pronova)
Unifat 54 (UPI)
Unifat 55L (UPI)
Stearyl Alcohol
 Empirical Formula $$C_{18}H_{38}O$$

Definition
Stearyl alcohol is the fatty alcohol that conforms generally to the formula:

$$CH_3(CH_2)_{16}CH_2OH$$

Technical Name
1-Octadecanol
Trade Names
Adol 63 (Witco)
Adol 61-NF (Witco)
Adol 62-NF (Witco)
Adol 620-NF (Witco)
Cachalot S-53 (Michel)
Cachalot S-54 (Michel)
Cachalot S-56 (Michel)
CO-1895 (Procter & Gamble)
Crodacol S-70 (Croda, Inc.)
Crodacol S-95 (Croda, Inc.)
Crodacol S-95 (Croda Chemicals, Inc.)
Fancol SA (Fanning)
Hyfatol 18-95 (Aarhus)
Hyfatol 18-98 (Aarhus)
Lanette 18 (Henkel)
Lanol S (SEPPIC)
Laurex 18 (Albright & Wilson)
Lipocol S (Lipo)
Stearal (Amerchol)
Stearyl Alcohol (Rhone-Poulenc)
Steraffine (Laserson & Sabetay)
Unihydag WAX-18 (UPI)
Palmitic Acid
 Empirical Formula $$C_{16}H_{32}O_2$$

Definition
Palmitic acid is the fatty acid that conforms generally to the formula:

$$CH_3(CH_2)_{14}COOH$$

Technical Name
n-Hexadecanoic acid
Trade Names
Crodacid PD3160 (Croda Universal Ltd.)
Edenor L2SM (Henkel)
Emersol 142 (Henkel/Emery)
Emersol 144 (Henkel/Emery)
Hystrene 7016 (Witco)
Hystrene 9016 (Witco)
Kartacid 1692 (Akzo BV)
Neo-Fat 16 (Akzo)
Neo-Fat 16-54 (Akzo)
Neo-Fat 16-56 (Akzo)
Neo-Fat 16-S (Akzo)
PRIFAC 2962 (Unichema)
Prifac 2690 (Unichema)
Trade Name Mixture
N.S.L.E. (Sederma)
Propylene Formula $$C_3H_8O_2$$

Definition
Propylene glycol is the aliphatic alcohol that conforms generally to the formula:

$$CH_3CH(OH)CH_2OH$$

Technical Name
1,2-Propanediol

Trade Names
Lexol PG-865 (855) (Inolex)
1,2-Propylene Glycol USP (BASF)
Xanthan Gum
  Definition
  Xanthan gum is a high molecular weight hetero polysaccharide gum produced by a pure-culture fermentation of a carbohydrate with Xathomonas campestris.
  Technical Names
  Corn sugar gum
Xanthan
  Trade Names
  Kelgum CG (Calgon)
  Keltrol (Kelco)
  Keltrol CG 1000 (Calgon)
  Keltrol CG BT (Calgon)
  Keltrol CG F (Calgon)
  Keltrol CG GM (Calgon)
  Keltrol CG RD (Calgon)
  Keltrol CG SF (Calgon)
  Keltrol CG T (Calgon)
  Keltrol CG TF (Calgon)
  Kelzon (Kelco)
  Merezan 8 (Meer)
  Merezan 20 (Meer)
  Rhodigel (Vanderbilt)
  Rhodigel (Rhone-Poulenc)
  Rhodopol SC (Rhone-Poulenc)
  Xanthan gum (Jungbunzlauer)
Triethanolamine
  Empirical Formula

Definition
  Triethanolamine is an alkanolamine that conforms generally to the formula:

Technical Names
  Ethanol, 2,2'2"-Nitrilotris-2,2',2"-Nitrilotris[Ethanol]
  TEA
Trolamine
  Trade Name
  Triethanolamine Pure C (BASF)

EXAMPLE

The typical formulation illustrated above is prepared commercially as follows:

| Ingredient | Batch | Units |
| --- | --- | --- |
| Purified water | 1084.47 | Gm |
| Urea USP | 1200.00 | Gm |
| Zinc (as bio-compatible salt) | 0.5 | Mg |
| Copper (as bio-compatible salt) | 0.5 | Mg |
| Manganese (as bio-compatible salt) | 0.5 | Mg |
| Carbopol 940 | 4.50 | Gm |
| Petrolatum | 178.20 | Gm |
| Mineral oil | 361.80 | Gm |

-continued

| Ingredient | Batch | Units |
| --- | --- | --- |
| Glyceryl stearate | 56.25 | Gm |
| Cetyl alcohol | 18.78 | Gm |
| Propylene glycol | 90.00 | Gm |
| Xanthan gum | 1.50 | Gm |
| Trolamine NF | 4.50 | Gm |

The above product was manufactured as follows:
Step 1
  Placed in Tank A and heated to 80–82° C. with constant stirring using a lightning mixer were the following:
  1069.47 Gm purified water
  1200.00 Gm urea
  After the urea dissolved added the zinc, copper and manganese salts and mixed to dissolve.
Step 2
  In a separate tank heated to 70–75° C. with constant stirring using a lightning mixer was placed:
  178.20 Gm petrolatum
  361.80 Gm mineral oil
  56.25 Gm glyceryl stearate
  18.78 Gm cetyl alcohol
Step 3
  Using a lightning mixer in Tank A, there was dispersed 4.50 Gm Carbopol 940 added in small increments.
Step 4
  The solution in Tank A was kept at 70–75° C., while stirring, by dispersing 90 Gm of propylene glycol and 1.5 Gm of xanthan gum. This was followed by the addition of 4.5 Gm of Trolamine, triethanolamine, and 15 Gm of purified water.
  When the oil phase in the second tank was completely melted, it was added to the first tank and mixing continued for approximately 15 minutes. The mixture was then cooled to about room temperature. The bulk product was sampled for testing and packaged into conventional containers for use as a cream. Other dosage forms can be made appropriate for topical applications including cutaneous wounds. In particular, a paste formulation is preferred for application on wounds.

We claim:

1. A dermatological composition comprising from about 21 to about 40 wt-% urea, and trace amounts of zinc, copper and manganese and the balance being dermatologically acceptable excipients.

2. The composition of claim 1 where zinc, copper and manganese are present as their pharmaceutically acceptable salts in an amount from about 1 ppm to 0.5 wt-%.

3. The composition of claim 2, wherein zinc, copper and manganese are present in an amount from about 10 ppm to about 0.2 wt-%.

4. The composition of claim 2, wherein the pharmaceutically acceptable salts are selected from the group consisting of acetates, bromides, carbonates, chlorides, citrates, gluconates, glycinates, glycerophosphates, lactates, iodides, nitrates, sulfates, and mixtures thereof.

5. The composition of claim 3, wherein the pharmaceutically acceptable salts are gluconates.

6. The composition of claim 1, wherein the excipients comprise skin protectants of an oleaginous nature derived from petroleum, emulsifiers and thickeners.

7. The composition of claim 6, wherein the skin protectants are a mixture of a semi-solid petrolatum or a synthetic oleaginous liquid derivative thereof, or a mixture thereof.

8. The composition of claim 6, wherein the semi-solid petrolatum is present in an amount from about 5.5 to about 20 wt-%.

9. The composition of claim 7, wherein the liquid petrolatum is present in an amount of from about 10 to about 20 wt-%.

10. The composition of claim 1, which further comprises up to 5 wt-% of propylene glycol.

11. The composition of claim 1, in the form of a semi-solid at room temperature.

12. A dermatological composition comprising:
  (a) about 21 to about 40 wt-% urea;
  (b) trace amounts of zinc, copper and manganese as their pharmaceutically acceptable salts;
  (c) about 5.5 to about 20 wt-% petrolatum or a synthetic or semi-synthetic hydrocarbon, or a semi-solid mixture thereof;
  (d) about 10 to about 20 wt-% of a liquid petrolatum or a synthetic or semi-synthetic oleaginous liquid fraction, or a mixture thereof;
  (e) about 0.25 to about 2 wt-% of a C16–18 aliphatic straight or branched chain fatty alcohol or fatty acid, or a mixture thereof;
  (f) about 1 to about 5 wt-% propylene glycol;
  (g) about 1 to about 3 wt-% glyceryl stearate;
  (h) about 0.01 to about 0.5 wt-% xanthan gum; and
  (i) the balance being water.

13. The composition of claim 12, wherein zinc, copper and manganese are present in an amount of about 1 ppm to about 0.5 wt-%.

14. The composition of claim 13, wherein zinc, copper and manganese are present in an amount from about 10 ppm to about 0.2 wt-%.

15. The composition of claim 12, wherein the pharmaceutically acceptable salts are selected from the group consisting of acetates, bromides, carbonates, chlorides, citrates, gluconates, glycinates, glycerophosphates, lactates, iodides, nitrates, sulfates, and mixtures thereof.

16. The composition of claim 15, wherein the pharmaceutically acceptable salts are gluconates.

17. The composition of claim 12, which further comprises a mixture of a carbomer and triethanolamine in a total amount from about 0.05 to about 30 wt-%.

18. The composition of claim 12, in the form of a semi-solid or gel.

19. A dermatological composition consisting essentially of:
  (a) about 21 to about 40 wt-% urea;
  (b) about 1 ppm to about 0.5 wt-% of zinc, copper and manganese as their pharmaceutically acceptable salts;
  (c) about 5.5 to about 20 wt-% petrolatum or a synthetic or semi-synthetic hydrocarbon, or a semi-solid mixture thereof;
  (d) about 10 to about 20 wt-% of a liquid petrolatum or a synthetic or semi-synthetic oleaginous liquid fraction, or a mixture thereof;
  (e) about 0.25 to about 2 wt-% of a C16–18 aliphatic straight or branched chain fatty alcohol or fatty acid, or a mixture thereof;
  (f) about 1 to about 5 wt-% propylene glycol;
  (g) about 1 to about 3 wt-% glyceryl stearate;
  (h) about 0.01 to about 0.5 wt-% xanthan gum;
  (i) about 0.05 to about 30 wt-% of a mixture of a carbomer and thiethanolamine; and
  (j) the balance being water.

20. The composition of claim 19, wherein zinc, copper and manganese are present in an amount from about 10 ppm to about 0.2 wt-%.

21. The composition of claim 19, wherein the pharmaceutically acceptable salts are gluconates.

22. The composition of claim 19, wherein component (c) is semi-solid petrolatum.

23. The composition of claim 19, wherein component (d) is mineral oil.

24. A method of treating skin disorders and cutaneous wounds comprising applying to an affected area an effective amount of a semi-solid dermatological composition comprising about 21 to about 40 wt-% urea, and trace amounts of zinc, copper and manganese present as their pharmaceutically acceptable salts.

25. A method of treating skin disorders and cutaneous wounds comprising administering to an affected area an effective amount of a dermatological composition according to claim 12.

26. A method of treating skin disorders and cutaneous wounds comprising administering to an affected area an effective amount of a dermatological composition according to claim 19.

* * * * *